United States Patent [19]

Schwartz

[11] Patent Number: 5,409,813
[45] Date of Patent: Apr. 25, 1995

[54] METHOD FOR MAMMALIAN CELL SEPARATION FROM A MIXTURE OF CELL POPULATIONS

[75] Inventor: Richard M. Schwartz, San Mateo, Calif.

[73] Assignee: SyStemix, Inc., Palo Alto, Calif.

[21] Appl. No.: 130,094

[22] Filed: Sep. 30, 1993

[51] Int. Cl.$^6$ .......................... C12N 5/00; C12Q 1/24; G01N 33/553

[52] U.S. Cl. .................................. 435/7.24; 210/660; 210/661; 210/695; 435/2; 435/30; 435/240.2; 436/526

[58] Field of Search ................. 435/2, 7.24, 30, 240.2; 436/526; 210/660, 661, 695

[56] References Cited

U.S. PATENT DOCUMENTS

| | | | |
|---|---|---|---|
| 4,675,113 | 6/1987 | Graves et al. | 210/635 |
| 4,714,680 | 12/1987 | Civin . | |
| 5,061,620 | 10/1991 | Tsukamoto et al. . | |
| 5,084,184 | 1/1992 | Burns . | |
| 5,130,027 | 7/1992 | Noble et al. . | |

FOREIGN PATENT DOCUMENTS

WO93/08268  4/1993  WIPO .

OTHER PUBLICATIONS

Burns et al., "Structural studies of a liquid-fluidized magnetically stabilized bed" *Chem. Eng. Comm.* (1988) 67:315–330.

Burns et al., "Application of magnetically stabilized fluidized beds to bioseparations" *React. Poly.* (1987) 6:45–50.

Lochmüller et al., "Affinity separations in magnetically stabilized fluidized beds: synthesis and performance of packing materials" *Sep. Sci. Technol.* (1987) 22:2111–2125.

Terranova et al., "Continuous cell suspension processing using magnetically stabilized fluidized beds" *Biotechnol. Bioengin.* (1991) 37:110–120.

Chetty et al., "Overcoming support limitations in magnetically stabilized fluidized bed separators" *Powder Technol.* (1991) 64:165–174.

Burns et al., "Continuous affinity chromatography using a magnetically stabilized fluidized bed" *Biotech. Prog.* (1985) 1:95–103.

Hu et al., "Study on the characteristics of a biological fluidized bed in a magnetic field" *Chem. Eng. Res. Des.* (1987) 65:238–242.

Chetty et al., "Continuous protein separations in a magnetically stabilized fluidized bed using nonmagnetic supports" *Biotechnol. Bioeng.* (1991) 38:963–971.

Department of the Navy Case 68,718 to Starken et al. (Sep. 25, 1985).

Visser, "Analysis and sorting of blood and bone marrow cells" *Flow Cytometry and Sorting*, 2nd Edition, Wiley–Liss, Inc., (1990) Chapter 33, pp. 669–683.

Reading et al., "Monoclonal antibody applications in bone marrow transplantation" *Biochem. Biophys. Acta.* (1986) 865:141–170.

*Primary Examiner*—David Saunders
*Attorney, Agent, or Firm*—Morrison & Foerster

[57] ABSTRACT

The invention provides a method for both the positive and negative selection of at least one mammalian cell population from a mixture of cell populations utilizing a magnetically stabilized fluidized bed. One desirable application of this method is the separation and purification of mammalian hematopoietic cells. Target cell populations include human stem cells.

26 Claims, 2 Drawing Sheets

METHOD FOR MAMMALIAN CELL SEPARATION FROM A MIXTURE OF CELL POPULATIONS

TECHNICAL FIELD

This invention relates to the use of a magnetically stabilized fluidized bed (MSFB) for selective affinity separation and purification of mammalian cell populations.

BACKGROUND ART

Separation of mixtures of chemicals, biomolecules and cell types is often effected by immunoaffinity chromatography. Packed beds, such as those used in column chromatography, are often used in affinity separation. However, problems such as non-specific trapping or filtration of cells and clogging make the use of a packed bed undesirable for cell separation. In addition, when fine particles are used to increase the mass transfer efficiency of packed beds, a large pressure drop across the bed often results. These problems require significant washing of the packed bed in order to flush contaminants and other cellular debris from the column.

One device that has been developed for reducing the pressure drop across a column of particles is the fluidized bed. A fluidized bed consists of solid particles and a gas or liquid which is passed upwardly through the particle bed with velocity sufficient to ensure that the drag forces of the fluid counterbalance the gravitational forces on the particle and cause random motion of the particles. The bed of particles will become fluidized and expand, resulting in a lower pressure drop across the fluidized bed as compared to the pressure drop across a packed bed of the same height. The fluidization of the bed also provides more surface contact between the particle and the fluid passing through the bed.

One disadvantage associated with fluidized beds is the radial and axial movement of the particles which result in significant intermixing of the particles. An advancement in fluidized bed technology is the magnetically stabilized fluidized bed (MSFB) which involves the use of a magnetic field and magnetizable particles to stabilize the bed. It has been found that, by supplying a magnetic field parallel to the path of fluid flow, the magnetizable particles can be locked in place, thus eliminating the intermixing of the particles.

In general, the MSFB combines some of the best characteristics of the fluidized bed with those of a fixed bed. More particularly, the MSFB provides a low pressure drop, the ability to transport solids through a system and good mass transfer driving force even as the fluid is depleted of its source. See Burns, Structural Studies of a Liquid-Fluidized Magnetically Stabilized Bed, *Chem. Eng. Comm*, 67:315–330 (1988). All documents cited herein are hereby incorporated by reference.

Because of these advantages, MSFBs have been used to separate various chemical species and proteins, and to filter yeast. For example, for the use of a MSFB to separate proteins see Burns, et al., Application of Magnetically Stabilized Fluidized Beds to Bioseparations, *Reactive Polymers*, 6:45–50 (1987) (human serum albumin); Lochmüller et al., Affinity Separations in Magnetically Stabilized Fluidized Beds: Synthesis and Performance of Packing Materials, *Separation Science and Technology*, 22:2111–2125 (1987) (trypsin); and U.S. Pat. No. 5,130,027, issued to Noble, Jul. 14, 1992, (Cytochrome-C). The use of a MSFB to separate various organic and inorganic compounds is discussed in U.S. Pat. No. 5,084,184 issued to Burns on Jan. 28, 1992. Finally, the use of an MSFB as a filter to collect yeast cells was reported by Terranova et al. Continuous Cell Suspension Processing using Magnetically Stabilized Fluidized Beds, *Biotechnology and Bioengineering*, 37:110–120 (1991). In this; latter reference, the filtration was not based on immunoaffinity but rather on electrostatic interaction between the positively charged nickel particles contained in the MSFB and the negatively charged yeast cells.

However, none of these references discuss the use of the MSFB for the affinity separation of mammalian cell population from a mixture of cell populations. The separation of a particular mammalian cell population from a mixture of cell populations is quite different from the separation of chemical species such as proteins from a solution. Most mammalian cells are on the order of 8 to 20 microns ($\mu$) in diameter. In contrast, the proteins and other chemical species which have been separated in a MSFB to date are significantly smaller, i.e. on the order of 1000 fold or more. Thus, the probability that the larger mammalian cell with greater fluid drag will bind to the particle and be retained is significantly lower under similar conditions. In addition, another factor unique to the separation of mammalian cells is the need to preserve cell viability.

In contrast to yeast cells, which are relatively insensitive to changes in osmolarity, pH and shear, higher order mammalian cells are much more sensitive to shear forces exerted during purification, pH osmolarity, and the chemical composition of the reagents used. Therefore, both the steps comprising the method and all reagents used must be non-toxic to the cells.

Mammalian hematopoietic (blood) cells provide a diverse range of physiological activities. Blood cells are divided into lymphoid, myeloid and erythroid lineages. The lymphoid lineages, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies, provides protection against neoplastic cells, scavenges foreign materials, produces platelets, and the like. The erythroid lineage provides the red blood cells, which act as oxygen carriers.

Despite the diversity of the nature, morphology, characteristics and function of the blood cells, it is presently believed that these cells are derived from a single progenitor population, termed "stem cells." Stem cells are capable of self-regeneration and may become lineage committed progenitors which are dedicated to differentiation and expansion into a specific lineage.

A highly purified population of stem cells is necessary for a variety of in vitro experiments and in vivo indications. For instance, a purified population of stem cells will allow for identification of growth factors associated with their self-regeneration. In addition, there may be as yet undiscovered growth factors associated (1) with the early steps of dedication of the stem cell to a particular lineage; (2) the prevention of such dedication; and (3) the negative control of stem cell proliferation.

Stem cells find use: (1) in regenerating the hematopoietic system of a host deficient in stem cells; (2) in a host that is diseased and can be treated by removal of bone marrow, isolation of stem cells and treatment of individuals with drugs or irradiation prior to re-engraftment of stem cells; (3) producing various hematopoietic cells; (4) detecting and evaluating growth factors relevant to stem cell self-regeneration; (5) the development of hematopoietic cell lineages and assaying for factors associated with hematopoietic development; and, is a target for gene therapy to endow blood cells with useful properties.

Highly purified stem cells are essential for hematopoietic engraftment including but not limited to that in cancer patients and transplantation of other organs in association with hematopoietic engraftment. Stem cells are important targets for gene therapy, where the inserted genes promote the health of the individual into whom the stem cells are transplanted. In addition, the ability to isolate the stem cell may serve in the treatment of lymphomas and leukemias, as well as other neoplastic conditions. Thus, there have been world-wide efforts toward isolating the human hematopoietic stem cell in substantially pure or pure form.

Stem cells constitute only a small percentage of the total number of hematopoietic cells. Hematopoietic cells are identifiable by the presence of a variety of cell surface protein "markers." Such markers may be either specific to a particular lineage or progenitor cell or be present on more than one cell type. Currently, it is not known how many of the markers associated with differentiated cells are also present on stem cells. One marker which was previously indicated as present solely on stem cells, CD34, is also found on a significant number of lineage committed progenitors. U.S. Pat. No. 4,714,680 describes a composition comprising human stem cells.

Hematopoietic cells are initially obtained as a mixture of a variety of cell populations ("mixture of cell populations"). The cell population to be purified or enriched for is termed herein the "target" cell population. Separation techniques involve successive purification steps relying on the use of affinity matrices to either retain nontarget cells and allow the target cells to flow through (negative selection) or to retain the target cells and allow the nontarget cells to flow through (positive selection).

Typically, hematopoietic cells are separated using negative selection affinity separations which are performed in a batch mode. For example, in processing a normal bone marrow (BM) harvest, it may be desirable to obtain only those cells exhibiting a specific cell surface antigen such as the CD34 antigen (CD34+ cells) which includes the stem cell population and a variety of other, more differentiated, cells. Typically, only approximately 0.1 to 5% of the total mononuclear cell population in a blood sample express the CD34 antigen. In contrast, cells expressing the CD15+ cell surface antigen, i.e. CD15 cells, which are more differentiated than stem cells, comprise approximately 50 to 75% of the total mononuclear cells.

In order to separate the target CD34+ cells from the mixture of cell populations by negative selection, the cell sample is placed in a vessel containing beads conjugated to an antibody specific to CD15. CD15+ cells bind to the anti-CD15 antibody and are then removed from solution by removal of the beads. Thus, by depleting the CD15+ cells, less than half to one quarter of the original cells, including the target CD34+ cells, remain for additional processing. Negative selection has been essential in separating stem and/or progenitor cells from BM or other sources since the target cells are present in such a low concentration.

In contrast, positive selection refers to a process in which the target cell population is bound to a particle having affinity for the target cell population and the nontarget cell populations do not bind and flow through. The target cell population is then obtained by releasing the cells from the particles and collecting the cells.

Because the target cell population typically comprises only a small fraction of the mixture of cell populations, positive selection would be the preferred process if it could be made efficient enough to selectively remove such a small percentage of cells. As noted earlier, CD34+ cells comprise only approximately 0.1 to 5% of the total mononuclear cell population. Of these cells stem cells comprise only a small percentage. Considering the time and reagents needed to stain and sort cells, it would be advantageous to directly select CD34+ cells for subsequent staining and sorting instead of successive purification of the mixture of cell populations that typically result from negative selection methods.

Until recently, positive selection of human hematopoietic cells has not been possible. One method which has been developed is the Ceprate LC ® system which uses a packed bed column and an avidin-biotin affinity system to select CD34+ cells. In this system, the avidin protein is attached to a bead or other solid support. The suspension containing the target CD34+ cells is mixed with a biotin-conjugated anti-CD34-antibody under conditions which allow the antibody to bind to CD34+ cells. This suspension is then passed downwardly through the column and, due to the affinity of the biotin to avidin, the CD34+ cells adhere to the support beads. After the entire suspension has passed through the column, the column is washed to remove any excess suspension or impurities. The support beads with the attached CD34+ cells are then agitated to physically separate the CD34+ cells from the beads. Although this method allows for positive selection of CD34+ cells, it also results in significant non-specific separation and therefore retention of nontarget cells, such as cancerous cells. It is believed that at least a portion of this contamination occurs due to filtration in the packed column.

Accordingly, it is an object of this invention to provide a method for both the positive and negative selection of mammalian hematopoietic cells that results in significantly less non-specific cell separation and filtration.

DISCLOSURE OF THE INVENTION

A method is provided for the selective enrichment of at least one mammalian target cell population from a suspension of a mixture of cell populations containing the target cell population and at least one nontarget cell population. The method comprises the steps of fluidizing a column containing a bed of magnetizable particles with a first solution, said particles comprising a substance having affinity for a specific population of mammalian cells; stabilizing the fluidized bed of magnetizable particles with a radially and axially substantially uniform magnetic field; and passing a suspension containing the mixture of cell populations through the fluidized, magnetically stabilized bed at a velocity at which at least one population of cells binds to said particles so as to be retained, thereby enriching the target cell population.

In one embodiment, a positive selection method is provided wherein the particles have affinity for the target cell population and the method additionally comprises the step of collecting the target cell population which are bound to the particles.

In another embodiment, a negative selection method is provided wherein the particles have affinity for the nontarget cell populations and the method additionally comprises the step of collecting the target cells which pass through the fluidized, magnetically stabilized bed.

Another embodiment provides a method for selectively, positively, separating at least one target mammalian cell population from a suspension of a mixture of cell populations containing the target cell population and at least one nontarget cell population. The method comprises the steps of fluidizing a column containing a bed of magnetizable particles with a solution, said particles comprising a substance having affinity for the target cell population; stabilizing the fluidized bed of magnetizable particles with a radially and axially substantially uniform magnetic field; passing a suspension containing the mixture of cell populations through the fluidized, magnetically stabilized bed at a velocity whereby the particles selectively bind the target cell population; and collecting the target cell population.

Another embodiment provides a method for negatively separating at least one mammalian cell population from a suspension of a mixture of cell populations containing the target cell population and at least one nontarget cell population. The method comprises the steps of fluidizing a column containing a bed of magnetizable particles with a solution, said particles comprising a substance having affinity for nontarget cells, stabilizing the bed of magnetizable particles with a radially and axially substantially uniform magnetic field, passing a suspension containing the mixture of cell populations through the fluidized, magnetically stabilized bed at a velocity whereby the particles bind the nontarget cell population, and collecting the target cell population which pass through the bed.

BEST MODE FOR CARRYING OUT THE INVENTION

Figure 1:
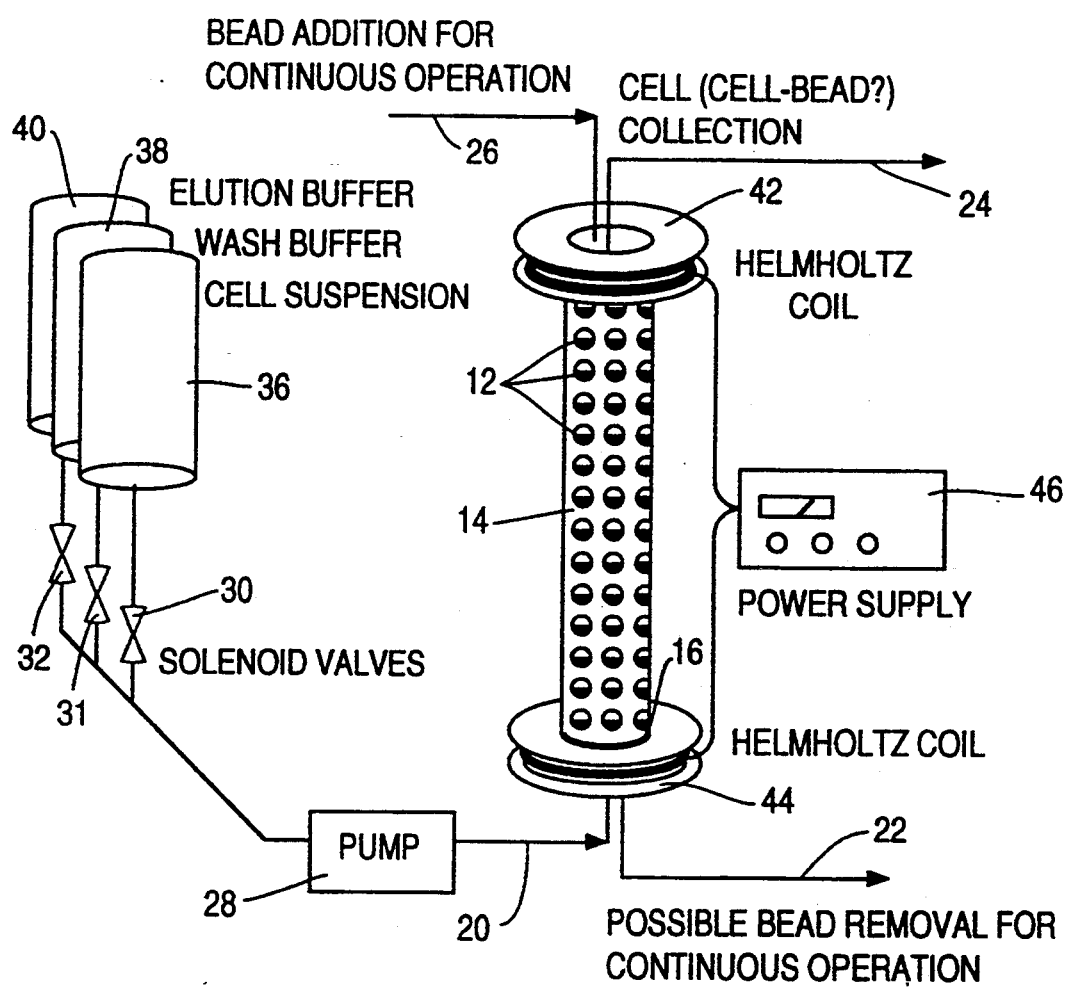
FIG. 1 shows a MSFB apparatus.

This invention is directed to a method for selectively separating at least one specific mammalian cell population from a mixture of cell populations. In this method, a protein, antibody, or other chemical substance having a specific affinity for at least one population of the mixture of cell populations is attached in any manner known in the art to magnetizable particles under conditions sufficient to allow binding of the specific cell population. The magnetizable particles are used in a MSFB and a suspension containing the mixture of cell populations is passed through the bed to bind the selected cell population to the particles.

As an aid in understanding this invention, the following definitions are provided. As used herein, the term "target cell population" denotes those cells which are desirably being purified or enriched. The term "positive selection" refers to a process in which the target cell population is purified or enriched by removing the target cell population from a mixture of cell populations by directly binding the target cell population to particles having affinity therefor. In contrast, the term "negative selection" refers to a process in which the target cell population is purified or enriched by removing nontarget cell populations from the mixture of cells by binding the nontarget cell populations to particles having affinity therefor.

This invention can be used to separate any type of mammalian cells. Preferably the cells are hematopoietic cells. More preferably they are human hematopoietic cells. Possible sources of hematopoietic cells include but are not limited to, bone marrow (BM), both adult and fetal; peripheral blood (PB), or fractions thereof; umbilical cord blood; and cadaveric bone marrow. In general, the cells may be derived from any mammalian organ including, but not limited to, the organs found in the gastrointestinal, circulatory, skeletal, muscular, nervous, skin, respiratory, and reproductive systems. Preferred organs include, but are not limited to, adult or fetal liver, kidney, and pancreas. A more preferred source of hematopoietic cells are bone marrow and peripheral blood.

A preferred target cell population is the human stem cell, as defined for instance in U.S. Pat. No. 5,061,620, the entirety of which is hereby incorporated by reference. Alternatively, a preferred target cell population is any hematopoietic stem cell or any cells that possess lymphoid, myeloid or erythroid characteristics. Another desirable target cell population is the hematopoietic progenitor cell.

Although the affinity binding chemistry used in this invention is specific for mammalian cells, the affinity binding can be between any of the generally known binding pairs including, but not limited to, antibodies and antigens; hormones and receptors; enzymes and either substrates, coenzymes, inhibitor activators; and its complement (a repressor or catabolite gene activator protein for double stranded DNA or the complement of a single strand of DNA); and messenger RNA and ribosomes. It is contemplated that this inventive method may be used for either positive or negative selection of cells.

The binding of the mammalian cells to the magnetizable particles can be through one or more binding moieties which are attached to the particles. For example, a linker may be attached to the particles which will specifically bind to an antibody that is specific to a specific mammalian cell.

Although this method can be used for the selective separation of any mammalian cells, one preferred use of this invention is for the positive selection of human hematopoietic cells. The selected hematopoietic cells could then be further purified using any suitable technique or placed in culture and expanded in number according to any suitable methods.

Although positive selection is a desired mode of operation, other modes of operation are also envisioned, including but not limited to negative selection, continuous, and series operation, all of which will be discussed in greater detail below.

THE MSFB

The MSFB used in this method is comprised of a column which is packed with magnetizable beads or other magnetizable particles, means for fluidizing the bed, and means for subjecting the bed to a magnetic field. The method of use is as described by the manufacturers with suitable modifications as described herein. A typical MSFB is shown in FIG. 1. As shown in FIG. 1, magnetizable beads or particles (12) are placed in a tubular column (14). A distributor plate or screen (16) having a plurality of apertures (18) which are smaller than the magnetizable particles is used for retaining the particles in the column and for distributing a fluid upwardly through the column. The bottom of the column is fitted with at least one piping connection (20) for placing a fluidizing medium in fluid communication with the column. Another connection (22) may be provided for removing the particles from the bottom of the bed.

Similarly, the top of the column is also fitted with at least one piping connection (24). This connection may be used for removing the fluidizing medium after it has passed through the bed. Alternatively, this connection could be used for washing the bed to remove cells which do not bind to the particles or to remove cells that have been released from the particles. Furthermore, this connection could be used for removing the particles, either with or without bound cells. Another piping connection (26) may be provided at the top of the column for the addition of particles to the top of the bed during continuous mode operation.

Means for forcing a fluid upwardly through the column are required for the operation of the MSFB. This may include at least one pump (28), at least one valve (30), (31), and (32), and piping (34) for connecting various fluids to the MSFB. As an alternative to a pump, a gravity-fed or pressurized tank may be used to drive the fluid through the MSFB. The fluids or solutions which may be passed through the MSFB may include the cell suspension containing the mixture of cell populations of mammalian cells (36), a wash solution (38), elution buffers (40), or other solutions such as a solution which is used to initially fluidize the bed before the cell suspension is passed through the bed. Such solutions are known in the art and should be isotonic, preferably sterile and preferably buffered to remain within a non-toxic pH range.

Means for subjecting the column of particles to a magnetic field is also required for the operation of the MSFB. A substantially uniform magnetic field may be created by any suitable means including, but not limited to, at least two coils which surround the column. As shown in FIG. 1, one embodiment includes a modified Helmholtz coil having an lapper coil (42) and a lower coil (44), both which surround the column. A power supply (46) is connected to both coils. Alternatively, a permanent magnet or any device which is capable of generating a substantially uniform magnetic field can be used in this invention.

The magnetic field should be substantially uniform in both the radial and axial directions along the length of the column. In addition, the strength of the magnetic field will depend on several characteristics of the magnetizable particles used, including the type and amount of magnetic material used and the size and density of the particles. A magnetic field in the range of 10 to 200 gauss is typically required to stabilize a fluidized bed. A determination of the suitable magnetic field strength is within the skill of one in the art.

The magnetizable particles for use in the MSFB can be made from a variety of solid support materials including, but not limited to, sepharose, sephadex, agarose and any other biologically inert material. Suitable magnetizable material includes, but is not limited to, magnetite, and nickel, iron, copper, cobalt and their alloys. Magnetite is the preferred material. The magnetizable material can be mixed with the support material and formed into particles. Ideally, the magnetizable material should comprise approximately 2 to 20% by weight of the total weight of the particle. Alternatively, magnetizable beads can be used in conjunction with separate non-magnetic particles. In this alternative configuration, the magnetic beads should comprise approximately 35 to 70% by volume of the total volume of particles in the column. See Chetty, "Overcoming Support Limitations in Magnetically Stabilized Fluidized Bed Separators", *Powder Technology*, 64:165–174 (1991).

The magnetizable particles must be designed to allow a fluidization velocity which will allow for binding of a specific mammalian cell population to the particles. In general, the fluidization velocity is a function of the diameter and density of the particle and the fluid density and viscosity. The fluidization velocity of particles must be calculated to insure that the flow rate required to fluidize the particles is not too high. Too high a flow rate will result in less binding and increased filtration of cells. A determination of the suitable fluidization velocity is within the skill of one in the art.

Another factor which must be considered when determining the appropriate particle size is the size of the cell to be bound to the particle. In this method, mammalian cells having a size in the range of approximately 8 to 20 microns ($\mu$) will desirably bind to the particle. One problem which may occur is that, if small particles are used, once the selected cell binds to the particle, the density of the combined cell/particle complex may be increased to a point where the cell/particle complex flows out of the column. One solution to this problem is to increase the magnetic field strength to hold the cell/particle complex in place. Alternatively, the cell/particle complex can be allowed to pass through the column and can be separated outside the column using a simple magnet or magnetic field.

Preferably the diameter of the particle is much greater than the diameter of the cell in order to increase the binding probability and capacity. In view of these factors, applicants have found that particles having a size in the range of 50 to 1000 microns and a density of less than 5 g/ml are suitable for mammalian hematopoietic cell separations. A preferred size is in the range of 50 to 300 microns and a preferred density is less than 2 g/ml.

OPERATION OF THE MSFB

In one embodiment of this invention, the MSFB is operated by first fluidizing the bed with a solution. Fluidization occurs when, at a specific flowrate, the fluid drag on the particles overcomes gravity and the particles lift off the bottom of the column. The solution used to initially fluidize the bed may be a wash solution or any other fluid. Once the bed is fluidized, the bed is subjected to a radially and axially substantially uniform magnetic field. The effect of the magnetic field can be thought of as creating a magnetic dipole in each particle, which causes each particle to remain fixed in place in a direction parallel to the magnetic field lines. Finally, once the bed is fluidized and magnetically stabilized, the suspension containing the mammalian cells is passed through the bed for separation. Those skilled in the art will recognize that it may be desirable to fluidize the bed using the cell suspension instead of using a different solution. Alternatively, it may be desirable to first magnetically stabilize the bed before fluidization.

As described above, the velocity at which the suspension is passed through the bed is limited by the ability of a specific mammalian cell to be sufficiently in contact with the particle so as to bind to that particle. In addition, the velocity must be low enough so that the cells are not removed by fluid drag from the particles. The fluidization of the bed allows for a constant velocity of the suspension through the bed, which also assists in the individual cells binding to the support particles.

When the suspension containing the mixture of cells is depleted or otherwise stopped, a wash solution may be passed through the column, if desired, to wash either bound or unbound cells from the bed. In addition, if a positive selection method was performed, the bound target cell population can be released by either physical or chemical methods.

If the viability of the cells is a concern, the bound cells must be separated from the particles using chemical methods that do not harm the cells. Examples of chemical methods include, but are not limited to, agents that reduce, oxidize, or otherwise chemically alter a chemical species, agents that effect a change in pH, or agents that change osmolality.

Blood cells are exquisitely sensitive to changes in pH, which must be carefully controlled to maintain cellular integrity. The normal pH of blood is 7.35–7.45. Nevertheless, a change in pH of the solutions in the fluidized bed may affect the affinity chemistry and decrease cellular adherence without killing the cells. Such a change in pH can be effected by adjusting the pH of a second elution buffer to be passed through the MSFB. In one example, the pH of the blood cell suspension is at about 7.25 and the pH of the second solution is at about 7.00. In another example, the pH of the blood cell suspension is at about 7.25 and the pH of the second solution is at about 6.80. In another example, the blood cell suspension has a normal pH, and the pH of the second solution is sufficiently low or high to permit release of the cell.

In a different example, the blood cell suspension has an elevated or depressed pH (for example, greater than 7.45 and less than 7.35, respectively), and the second solution has a normal pH. These values can be adjusted by routine experiments by those skilled in the art, to maintain cell viability and increase selectivity. After the bound cells are released, the pH of the cell suspension is adjusted to normal by the addition of the appropriate dilute acid or base. In addition, the cell suspension may be buffered using any suitable physiologically acceptable buffers including, but not limited to, any dibasic or monobasic phosphate saline, sodium bicarbonate, phosphate buffered saline (PBS), and (N-[2 Hydroxy-ethyl]-piperazine-N'-[2-ethanesulfonic acid] (HEPES).

Chemical separation may also include competitive binding techniques or chemical alteration of the substance which binds the mammalian cell to the particle.

Physical separation methods may include decreasing or otherwise stopping the magnetic field to allow radial and axial movement of the particles in the bed. The resulting Brownian motion will result in release of the bound cells from the particles. Alternatively, the velocity of a second solution, most probably a wash solution or elution buffer may be increased significantly to permit large enough hydrodynamic shear forces to separate the cell from the particles. Furthermore, a combination of decreasing the magnetic field and passing a second solution through the bed at an increased velocity may be used to allow the combination of random motion and shear forces to separate the bound cells from the particles.

This MSFB system, as described above, could have significant advantages in positive selection. This method does not result in significant non-specific cell separation because the contaminants are not trapped by the bed of particles. Because of the fluidization of the bed of particles, only those mammalian cells having affinity for the binding substance attached to the particle will bind to the particle. The remaining cells will pass through the bed and can be collected for disposal, additional separations or other processing, as desired. This method also allows for very high efficiency capture of a positively selected population with minimal losses. This significantly decreases the necessity for downstream purification, if desired, due to the increased purity of the sample.

MODES OF OPERATION

Several possible modes of operation of a MSFB with specific application to BM or PB are contemplated. These include:

(a) Target cell populations, for example CD34+ cells, could be positively selected by binding to particles in the MSFB while the non-target cells pass through the MSFB and are discarded. The particles could be washed by flowing a wash buffer through the fluidized, magnetically stabilized bed, if required. The selected target cell population could then be eluted from the fluidized, magnetically stabilized bed using the appropriate elution buffer. The collected cells could then be recovered from the elution buffer.

(b) A negative selection mode could be used to bind nontarget cell populations to the magnetizable particles in the MSFB. Examples of cells which are suitable for a negative selection method include, but are not limited to, the mature cell lineage panel having markers including, but not limited to, CD2, CD14, CD15, CD19. An example of lineage specific markers is presented in Table 1. These mature nontarget cells would bind to the particles while the target cell population passes through to be collected. The particles in the MSFB could then be washed with buffer and the additional target cell population collected.

Table 1 summarizes probable phenotypes of stem cells in fetal, adult, and mobilized peripheral blood. In Table 1 myelomonocytic stands for myelomonocytic associated markers, NK stands for natural killer cells and AMPB stands for adult mobilized peripheral blood. As used herein both infra, supra and in Table 1, the negative sign or, uppercase negative sign, (−) means that the level of the specified marker is undetectable above Ig isotype controls; by FACS analysis, and includes cells with very low expression of the specified marker.

TABLE 1

| Probable Stem Cell Phenotypes | | | | | | | | |
|---|---|---|---|---|---|---|---|---|
| NK and T cell markers | | | B cell markers | | | Myelomonocytic | | |
| CD2 | CD3 | CD8 | CD10 | CD19 | CD20 | CD14 | CD15 | CD16 |

TABLE 1-continued

| | | | | | | | | |
|---|---|---|---|---|---|---|---|---|
| FBM | — | — | — | — | — | — | — | — | — |
| ABM | — | — | — | — | — | — | — | — | — |
| AMPB | — | — | — | — | — | — | — | — | — |

| | Probable Stem Cell Phenotypes | | | | | | | |
|---|---|---|---|---|---|---|---|---|
| | | | | Other | | | | |
| | CD33 | CD34 | CD38 | HLA-DR | C-Kit | Thy | Rho | P-gp Activity |
| FBM | ? | + | — | + | + | + | lo | + |
| ABM | — | + | ? | lo/— | + | + | lo | + |
| AMPB | lo/—? | + | ? | lo/— | ? | + | lo | + |

(c) The MSFB could be run in batch mode, or in continuous mode by continually supplying particles into the top (or other point) of the column and removing them from the column bottom (or other point). This would allow use of a small column to process a whole BM aspirate or PB apheresis.

(d) For a negative selection, binding substances having affinity for the mature cell lineage panel could be attached to the particles in a single MSFB. Alternatively, a plurality of binding substances each having affinity for a different mature cell could be used individually in a series of MSFBs with the cell suspension flowing sequentially through the various MSFBs.

(e) "Prepackaged" sets of MSFB columns could be linked together in series or parallel for any combination of selections. For example, a series of MSFB columns could be used in a negative selection mode to sequentially remove a series of nontarget cells. Alternatively, a set of MSFB columns could be used in either series or parallel to positively select a group of target cell populations by binding these different target cell populations to particles in the various prepackaged MSFB columns. Finally, a set of MSFB columns could be used in series or parallel to both positively and negatively select any number of cells. These various combinations of prepackaged MSFB columns will allow for very simple patient-specific cell selection/removal.

Figure 2:
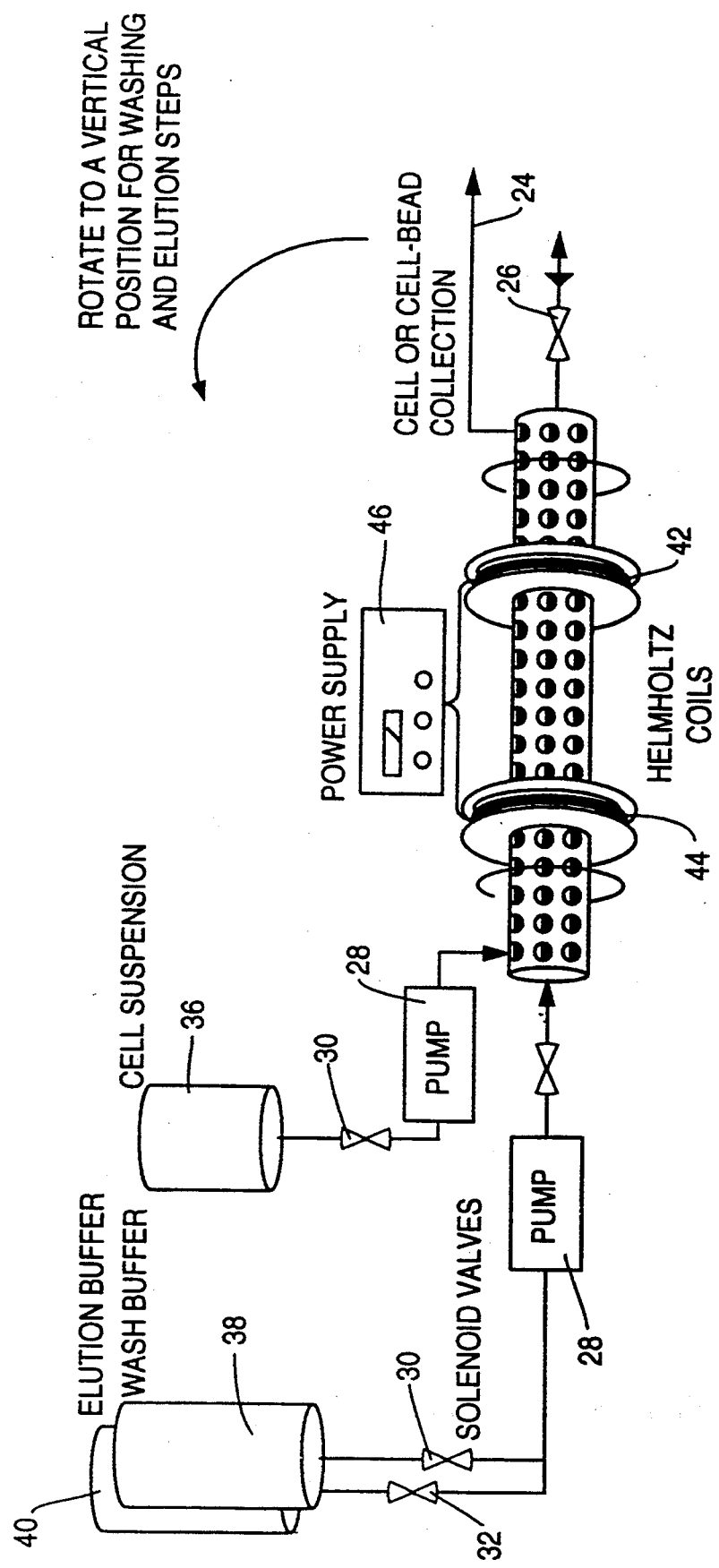
FIG. 2 shows a horizontally rotated MSFB for batch cell collection prior to washing and cell removal.

(f) Alternatively, for batch mode separation, the MSFB could be filled with particles and cells and slowly rotated to a horizontal position. The magnetic field is not activated during the actual selection step, in which the cells contact and adhere to the particles for capture. The MSFB could then be rotated to a vertical position and the magnetic field activated to recover the cells in a typical MSFB mode. This is depicted in FIG. 2.

This system has the potential to significantly improve the debulking of BM or PB harvests by either the positive selection of a target cell population or the negative selection of cells other than the desired target cell population. In addition, because this method can be used for positive selection of a target cell population, the time and reagents needed for later processing, such as staining and sorting of the cells, can be drastically reduced.

The invention now being fully described, it will be apparent to one of ordinary skill in the art that many changes and modifications can be made thereto without departing from the spirit or scope of the claims set forth below.

I claim:

1. A method for selectively separating at least one mammalian target cell population from a suspension of a mixture of cell populations wherein the suspension contains the target cell population and at least one non-target cell population, said method comprising the steps of:
   fluidizing a column containing a bed of magnetizable particles with a first solution, said particles comprising a substance having affinity for said target cell population;
   stabilizing said fluidized bed of magnetizable particles with a radially and axially substantially uniform magnetic field;
   passing said suspension through said fluidized, magnetically stabilized bed at a velocity whereby said particles bind said target cell population; and
   collecting said target cell population.

2. The method according to claim 1 wherein said mixture of cell populations are selected from the group consisting of fetal bone marrow, adult bone marrow, peripheral blood, fractions of peripheral blood, fetal liver, adult liver, fetal kidney, adult kidney, fetal pancreas, and adult pancreas cells.

3. The method according to claim 1 wherein said mixture of cell populations is derived from a mammalian organ.

4. The method according to claim 1 wherein said target cell population comprises human hematopoietic stem cells.

5. The method according to claim 1 wherein said target cell population comprises human hematopoietic progenitor cells.

6. The method according to claim 1 wherein said target cell population possesses hematopoietic, lymphoid, myeloid, or erythroid characteristics.

7. The method according to claim 1 wherein said collecting step further comprises the step of releasing said target cell population from said particles by physical means.

8. The method according to claim 7 wherein said releasing comprises decreasing said magnetic field to allow Brownian motion of said particles to separate the bound cells from said particles.

9. The method according to claim 7 wherein said releasing comprises passing a second solution through said bed of particles and increasing the velocity of said second solution to permit shear forces to separate the bound cells from said particles.

10. The method according to claim 9 wherein said physical releasing further comprises decreasing said magnetic field to allow radial and axial movement of said particles.

11. The method according to claim 1 wherein said collecting step further comprises the step of releasing said target cell population from said particles by chemical means.

12. The method according to claim 11 wherein said releasing comprises passing a second solution having a pH different from said suspension through said bed of particles.

13. The method according to claim 11 wherein said chemical releasing comprises competitive inhibition binding with molecules which compete with said target cell population.

14. The method according to claim 1 wherein said magnetizable particles are in the range of 50 to 1000 microns and have a density less than 5 g/ml.

15. The method according to claim 14 wherein said magnetizable particles are in the range of 50 to 300 microns and have a density less than 2 g/ml.

16. A method for selectively separating at least one target mammalian cell population from a suspension of a mixture of cell populations wherein the suspension contains: the target cell population and at least one nontarget cell population, said method comprising the steps of:
fluidizing a column containing a bed of magnetizable particles with a first solution, said particles comprising a substance having affinity for the nontarget cell populations;
stabilizing said fluidized bed of magnetizable particles with a radially and axially substantially uniform magnetic field;
passing said suspension through said fluidized, magnetically stabilized bed of particles at a velocity whereby said particles bind at least one nontarget cell population; and
collecting said target cell population which passes through said bed.

17. The method according to claim 16 wherein said mixture of cell populations is selected from the group consisting of fetal bone marrow, adult bone marrow, peripheral blood, fractions of peripheral blood, fetal liver, adult liver, fetal kidney, adult kidney, fetal pancreas, and adult pancreas cells.

18. The method according to claim 16 wherein said mixture of cell populations is derived from a mammalian organ.

19. The method according to claim 16 wherein said target cell population comprises human hematopoietic stem cells.

20. The method according to claim 16 wherein said target cell population comprises human hematopoietic progenitor cells.

21. The method according to claim 16 wherein said target cell population possesses hematopoietic, lymphoid, myeloid, or erythroid characteristics.

22. The method according to claim 16 wherein said magnetizable particles are in the range of 50 to 1000 microns and have a density less than 5 g/ml.

23. The method according to claim 22 wherein said magnetizable particles are in the range of 50 to 300 microns and have a density less than 2 g/ml.

24. A method for the selective enrichment of at least one mammalian target cell population from a suspension of a mixture of cell populations wherein said suspension contains said target cell population and at least one nontarget cell population, said method comprising the steps of:
fluidizing a column containing a bed of magnetizable particles with a first solution, said particles comprising an antibody having affinity for a specific population of mammalian cells;
stabilizing said fluidized bed of magnetizable particles with a radially and axially substantially uniform magnetic field; and
passing the suspension through said fluidized, magnetically stabilized bed at a velocity at which at least one specific population of cells binds to said particles thereby enriching the target cell population.

25. The method according to claim 24 wherein said particles have affinity for said target cell population and the method further comprises the step of collecting said target cell population bound to said particles.

26. The method according to claim 24 wherein said particles have affinity for said nontarget cell population and the method further comprises the step of collecting said target cells which pass through said fluidized, magnetically stabilized bed.

* * * * *